United States Patent
Dhindsa (10) Patent No.: US 6,743,237 B2
(45) Date of Patent: Jun. 1, 2004

(54) ENDOSCOPIC STONE EXTRACTION DEVICE WITH IMPROVED BASKET

(75) Inventor: Avtar S. Dhindsa, Valparaiso, IN (US)

(73) Assignee: Innon Holdings, LLC, Valparaiso, IN (US)

(*) Notice: Subject to any disclaimer, the term of this patent is extended or adjusted under 35 U.S.C. 154(b) by 184 days.

(21) Appl. No.: 10/022,061

(22) Filed: Dec. 12, 2001

(65) Prior Publication Data

US 2002/0095161 A1 Jul. 18, 2002

Related U.S. Application Data

(63) Continuation-in-part of application No. 09/761,786, filed on Jan. 17, 2001, now Pat. No. 6,551,327.

(51) Int. Cl.$^7$ .............................................. A61B 17/22
(52) U.S. Cl. ...................................................... 606/127
(58) Field of Search ........................ 606/110, 113–115, 606/127, 128, 159, 200

(56) References Cited

U.S. PATENT DOCUMENTS

| | | |
|---|---|---|
| 3,955,578 A | 5/1976 | Chamness et al. |
| 4,557,255 A | 12/1985 | Goodman |
| 4,590,938 A | 5/1986 | Segura |
| 4,612,931 A | 9/1986 | Dormia |
| 4,927,426 A | 5/1990 | Dretler |
| 5,066,295 A | 11/1991 | Kozak et al. |
| 5,190,542 A | 3/1993 | Nakao et al. |
| 5,192,286 A | 3/1993 | Phan |
| 5,197,968 A | 3/1993 | Clement |
| 5,201,740 A | 4/1993 | Nakao et al. |
| 5,397,320 A * | 3/1995 | Essig et al. .................... 606/37 |
| 5,417,697 A | 5/1995 | Wilk et al. |
| 5,496,330 A | 3/1996 | Bates |
| 5,535,759 A * | 7/1996 | Wilk .......................... 128/898 |
| 5,788,710 A | 8/1998 | Bates |
| 5,910,154 A | 6/1999 | Tsugita et al. |
| 5,911,734 A | 6/1999 | Tsugita et al. |
| 5,957,932 A | 9/1999 | Bates |
| 5,989,266 A | 11/1999 | Foster |
| 6,007,546 A * | 12/1999 | Snow et al. ................. 606/113 |
| 6,015,415 A | 1/2000 | Avellanet |

(List continued on next page.)

OTHER PUBLICATIONS

"Endoscopic Stone Extraction Device with Improved Basket," U.S. patent application Ser. No. 09/761,786, filed Jan. 17, 2001; inventor: Avtar S. Dhindsa.

"Endoscopic Stone Extraction Device with Rotatable Basket," U.S. patent application Ser. No. 09/761,785, filed Jan. 17, 2001; inventor: Avtar S. Dhindsa.

"Endoscopic Stone Extraction Device with Rotatable Basket," U.S. patent application Ser. No. 09/870,348, filed May 30, 2001; inventor: Avtar S. Dhindsa.

Dretler, Stephen P., "The Stone Cone: A New Generation of Basketry", The Journal Of Urology, vol. 165, May 2001, pp. 1593–1596.

*Primary Examiner*—Kevin Shaver
*Assistant Examiner*—Michael B. Priddy
(74) *Attorney, Agent, or Firm*—Brinks Hofer Gilson & Lione (57) ABSTRACT

An endoscopic stone extraction device includes a handle that supports a sheath, and a filament such as a wire slidably disposed in the sheath. One end of the wire is mounted to the handle for rotation with respect to the handle and the other end of the handle supports a stone extraction basket. A manipulator is provided on the wire to allow a user to rotate the filament and therefore the basket with respect to the handle. The basket can have a side-facing opening or a rear-facing opening. In either case, a stone retention region is provided with relatively small openings sized to retain stones smaller than two millimeters in diameter. A collapsible rake is disclosed which facilitates the collection and extraction of stone fragments.

17 Claims, 7 Drawing Sheets

U.S. PATENT DOCUMENTS

| | | |
|---|---|---|
| 6,027,520 A | 2/2000 | Tsugita et al. |
| 6,042,598 A | 3/2000 | Tsugita et al. |
| 6,059,796 A | 5/2000 | Bilitz |
| 6,077,274 A | 6/2000 | Ouchi |
| 6,093,196 A | 7/2000 | Okada |
| 6,096,053 A | 8/2000 | Bates |
| 6,099,534 A | 8/2000 | Bates |
| 6,165,179 A | 12/2000 | Cathcart et al. |
| 6,165,200 A | 12/2000 | Tsugita et al. |
| 6,168,603 B1 | 1/2001 | Leslie et al. |
| 6,190,394 B1 | 2/2001 | Lind et al. |
| 6,216,044 B1 | 4/2001 | Kordis |
| 6,235,026 B1 | 5/2001 | Smith |
| 6,245,089 B1 | 6/2001 | Daniel et al. |
| 6,270,513 B1 | 8/2001 | Tsugita et al. |
| 6,346,116 B1 | 2/2002 | Brooks et al. |
| 6,419,679 B1 * | 7/2002 | Dhindsa ............... 606/127 |
| 6,494,885 B1 * | 12/2002 | Dhindsa ............... 606/127 |
| 6,673,080 B2 * | 1/2004 | Reynolds et al. ........ 606/127 |
| 2001/0041909 A1 | 11/2001 | Tsugita et al. |

* cited by examiner

ENDOSCOPIC STONE EXTRACTION DEVICE WITH IMPROVED BASKET

CROSS REFERENCE TO RELATED APPLICATION

This application is a continuation-in-part of U.S. patent application 09/761,786, filed Jan. 17, 2001, now U.S. Pat. No. 6,551,327 the entirety of which is hereby incorporated by reference.

BACKGROUND

The present invention relates to basket-type devices for extracting stones such as ureteral stones, calaceal stones and other calculus and the like from the renal or biliary systems.

Various types of stone extraction baskets have been used in the past to extract stones and stone fragments from various biological systems. See for example the devices shown in the following U.S. Patents: Bates U.S. Pat. No. 6,099,534, Okada U.S. Pat. No. 6,093,196, Ouchi U.S. Pat. No. 6,077,274, Bilitz U.S. Pat. No. 6,059,796, Foster U.S. Pat. No. 5,989,266, Bates U.S. Pat. No. 5,957,932, Bates U.S. Pat. No. 5,788,710, Bates U.S. Pat. No. 5,496,330, Dormia U.S. Pat. No. 4,612,931, and Segura U.S. Pat. No. 4,590,938.

A typical stone extraction basket includes a wire basket carried by one end of a wire that is received within the lumen of a sheath. The end of the wire opposite the basket is secured to a handle that is used to slide the sheath over the wire, thereby moving the basket into and out of the lumen of the sheath. When the basket is out of the sheath, it expands to receive a stone. The sheath is then moved toward the basket to reduce the size of the basket openings, and the basket and the enclosed stone are removed from the body.

Recently, ultrasonic, laser, and electro-hydraulic techniques have been used to fragment stones in situ. Typically, the stone fragments are left in the body to be excreted. However, in some cases stone fragments may not be excreted as quickly or as completely as desired. Conventional stone extraction baskets are not optimized for the extraction of shattered stone fragments. Thus, a need presently exists for an improved endoscopic stone extraction device that is easier to use and better suited for the extraction of stone fragments.

SUMMARY

The preferred embodiments described below include a new type of stone extraction basket that is well suited to the collection of small stone fragments.

In one embodiment, the stone extraction basket has a large, side-facing opening to admit stones and stone fragments into the interior of the basket, and over half of the surface area of the basket is provided with relatively small openings adapted to retain stones and stone fragments in the basket. In another embodiment, the large openings of the basket are oriented to face the sheath, and the stone retention portion of the basket is disposed opposite the sheath.

The handle described below allows the basket to be rotated inside the body, as for example to orient the basket to admit a stone into the basket. The improved basket designs described below facilitate the retention and extraction of small stone fragments.

The foregoing section has been provided by way of general introduction, and it should not be used to narrow the scope of the following claims.

DETAILED DESCRIPTION OF THE PRESENTLY PREFERRED EMBODIMENTS

Figure 1:
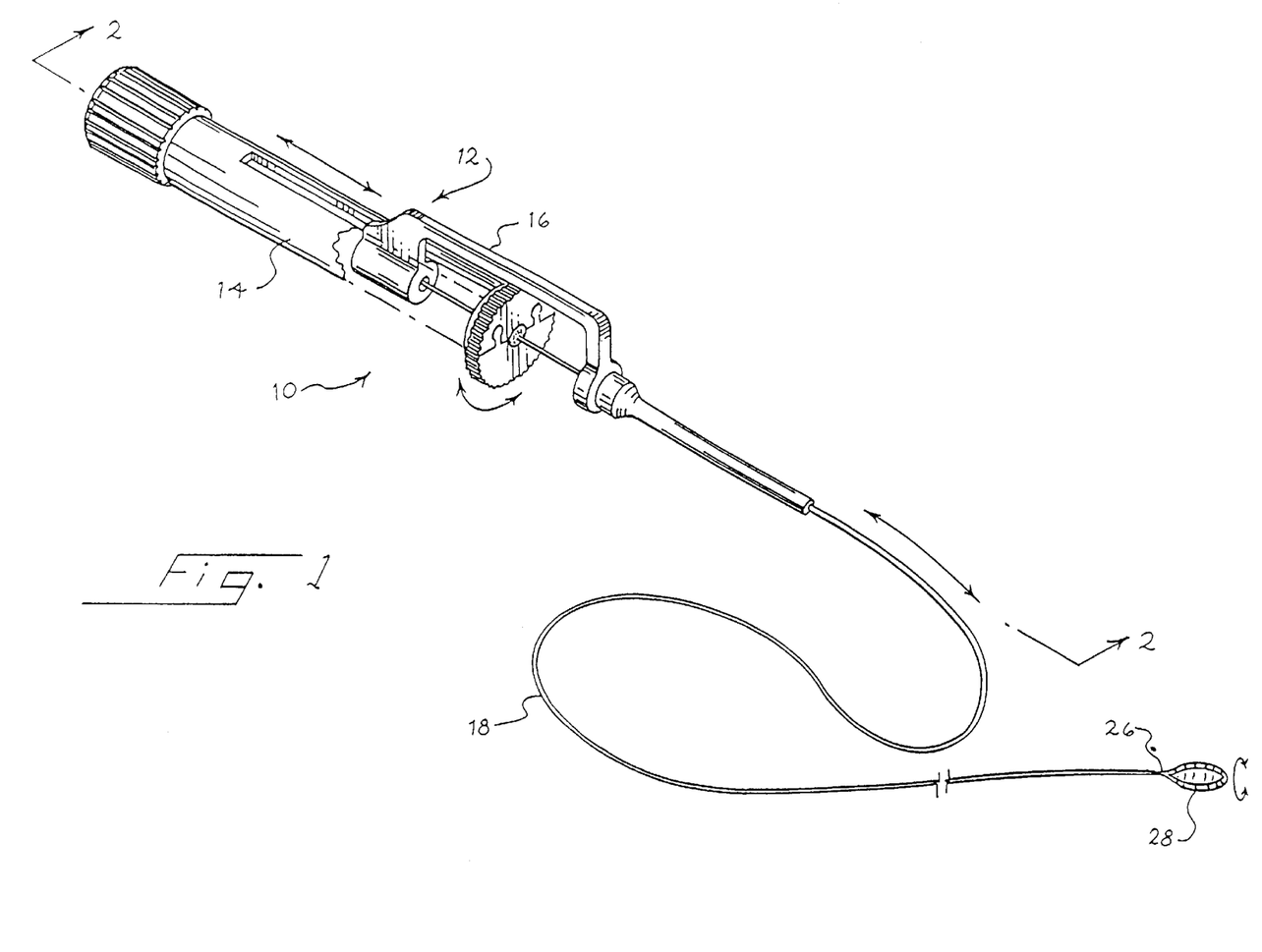
FIG. 1 is a perspective view of an endoscopic stone extraction device that incorporates a preferred embodiment of this invention.

Turning now to the drawings, FIG. 1 shows an endoscopic stone extraction device 10 that incorporates a preferred embodiment of this invention. The device 10 includes a handle 12 that in turn includes a grip 14 and a slide 16. As explained in greater detail below, the slide 16 is mounted to slide longitudinally along the length of the grip 14.

A tubular sheath 18 is secured to the slide 16. The sheath 18 defines a lumen 19, and the sheath 18 can be formed of any suitable flexible material, including the materials described in the above-identified prior-art patents. A strain relief collar 20 is provided at the point where the sheath 18 is secured to the slide 16 to reduce the incidence of kinking.

The device also includes a filament 22 having a first end 24 (FIG. 2) and a second end 26 (FIG. 1). The first end 24 is rotatably secured to the grip 14 (FIG. 2), and the second end 26 supports a stone extraction basket. The filament 22 can be formed of any suitable material, and is typically formed of a flexible metallic wire. Preferably, the first end 24 is thicker and stiffer than the second end 26 to facilitate insertion and manipulation of the basket 28.

The following sections will first describe the handle 12 in greater detail, to before turning to alternative forms of the basket 28.

The Handle 12

Figure 2:
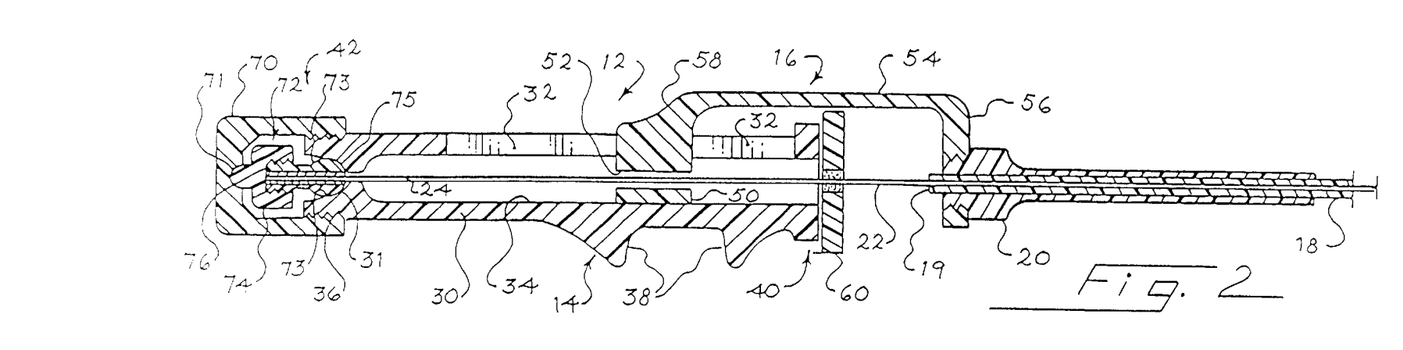
FIG. 2 is a cross-sectional view taken along line 2—2 of FIG. 1.

As best shown in FIG. 2, the handle 12 includes a tube 30 that defines a longitudinally extending slot 32. The tube 30 forms a bore 34 and terminates at one end in external threads 36. Protruding elements 38 extend away from the perimeter of the tube 30 to facilitate the grasping of the tube 30 by a physician during use. For purposes of discussion, the portion of the tube 30 adjacent the external threads 36 will be referred to as the rear portion 42, and the opposite end of the tube 30 will be referred as the front portion 40. The tube 30 may for example be formed of any suitable, moldable thermoplastic material, though the widest variety of materials can be adapted for use with this invention.

Continuing with FIG. 2, the slide 16 includes a guide cylinder 50 sized to slide along the bore 34 of the tube 30. This guide cylinder 50 defines a central opening 52 sized to pass the filament 22 with little or no friction therebetween. The slide 16 also includes an arm 54 that extends from the guide cylinder 50 through the slot 32 to a plate 56. The arm 54 holds the plate 56 in alignment with the centerline of the tube 30. The slide 16 includes a gripping portion 58 that can be pushed or pulled by a physician during use to move the slide 16 along the longitudinal axis of the tube 30. As before, a wide range of materials can be used for the slide 16, including any suitable thermoplastic material.

Figures 3, 4, 5, 6, 6A:
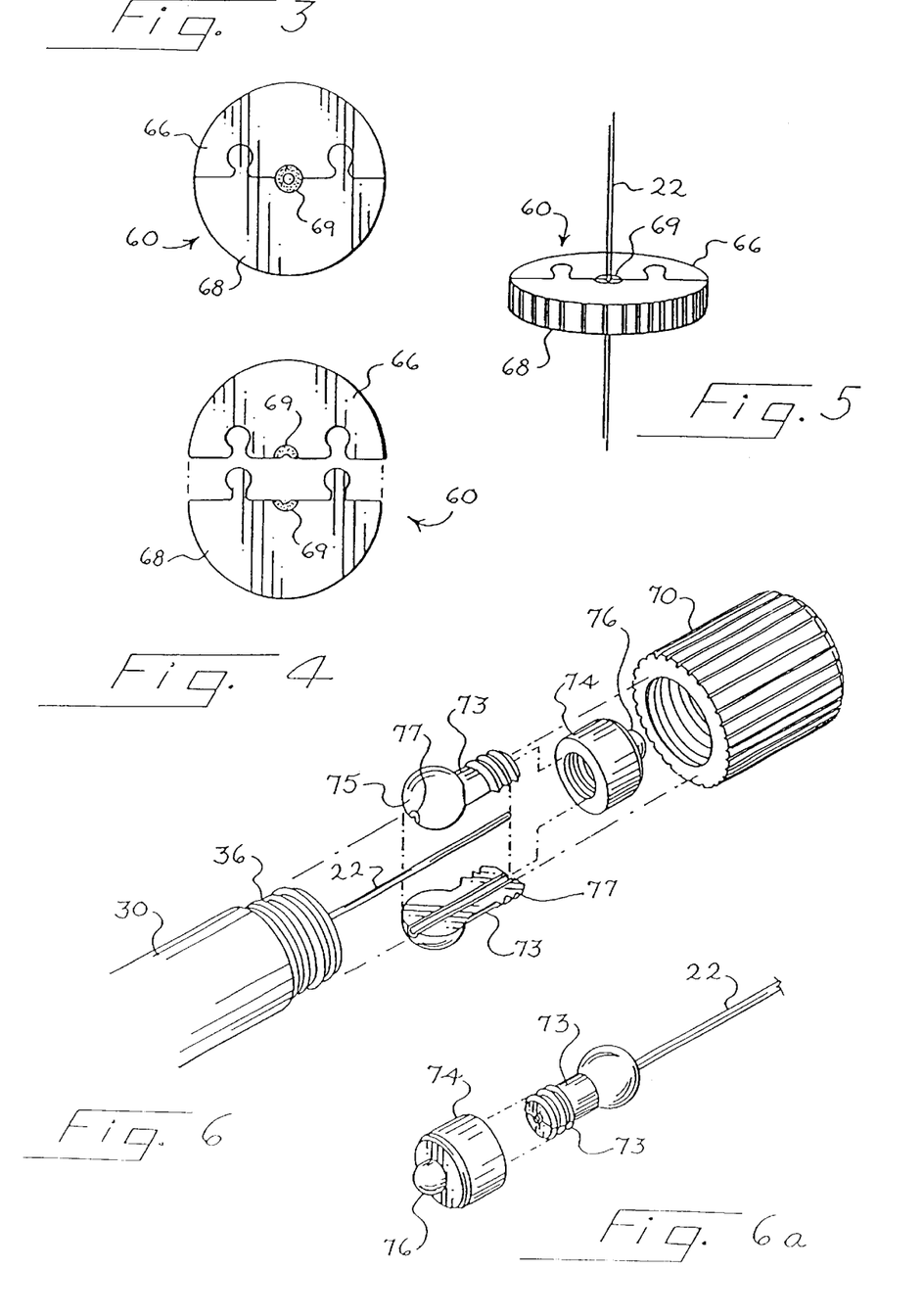
FIGS. 3, 4 and 5 are detailed views of a thumb wheel included in the embodiment of FIGS. 1 and 2.
FIG. 6 is an exploded perspective view of a portion of the handle and the end portion of the wire of the embodiment of FIGS. 1 and 2.
FIG. 6a is an exploded perspective view of the elements 73, 74 of FIG. 6 from another viewing angle.

As shown in FIGS. 1–5, a disk 60 is provided. This disk 60 is positioned adjacent the front portion 40 of the tube 30. The disk 60 is clamped onto the filament 22, and the disk 60 is rotatable with respect to both the tube 30 and the slide 16. As shown in FIGS. 3–5, the disk 60 includes half-disks 66, 68 that snap together in a releasable manner. The half-disks 66, 68 carry respective elastomeric gripping portions 69 designed to grip the filament 22 therebetween when the half-disks 66, 67 are snapped together.

As best shown in FIGS. 1, 2, 6 and 6a, the handle 12 carries a threaded cap 70 that defines a set of internal threads sized to mate with the external threads 36. The cap 70 includes a socket 71 that bears on a chuck 72. When the cap 70 is tightened in place, the chuck 72 is held between the socket 71 and an internal socket 31 formed by the tube 30. The chuck 72 is free to rotate but not to translate with respect to the tube 30.

The chuck 72 includes two parts 73, each having a central groove 77 sized to clamp against the filament 22. The groove 77 may be lined with an elastometric layer to ensure good frictional contact between the chuck 72 and the filament 22. Each part 73 defines external threads, and the parts 73 are clamped against the filament by a cap nut 74 such that the chuck 72 rotates and translates in unison with the filament 22. The chuck 72 forms a convex surface 75 that engages the socket 31, and a convex surface 76 that engages the socket 71. The surfaces 75, 76 are shaped to allow low-friction rotation of the chuck 72 and the filament 22 relative to the tube 30. Thus, the chuck 72 and associated elements carried by the tube 30 form a rotational joint. Other types of rotational joints may be used, including ball-and-socket joints. For example, a ball-and-socket joint may be included in the filament 22 near the first end 24, and the first end 24 may be fixed to the tube 30. Also, the filament may have an enlarged end that forms part of the rotational joint, and the enlarged end may be sized to fit through the lumen of the sheath 18. Alternatively, the enlarged end may be too large to fit through the lumen of the sheath, and may be removable from the body of the filament 22, e.g. by disassembling the enlarged end from the filament 22.

In use, the device 10 is assembled as shown in FIGS. 1 and 2. Initially, the slide 16 is advanced (i.e. moved to the right in the view of FIG. 2) to move the sheath 18 over the basket 28. This reduces the cross-sectional dimensions of the basket 28 and facilitates insertion of the basket 28 into a region of the body adjacent to the stone to be removed. The slide 16 is then moved to the left in the view of FIG. 2 to expose the basket 28, which resiliently assumes an enlarged operational shape. As described in greater detail in the following section relating to the basket, the basket defines one or more large, stone-receiving openings, and in some embodiments the stone-receiving openings are laterally facing. The physician can position the basket as desired by manipulating the disk 60, thereby rotating the filament 22 and the attached basket 28.

It should be apparent from the foregoing discussion that rotation of the disk 60 and the filament 22 occurs without rotation of the sheath 18, the slide 16 or the handle 12. This arrangement facilitates rotation of the filament 22 and the basket 28 inside the lumen of the body cavity in which it is inserted, since friction between the sheath 18 and the endoscopic device and between the sheath 18 and adjacent tissue do not impede rotation of the filament 22 and the basket 28. Rotation of the filament 22 is guided by the rotational joint that includes the chuck 72. Once a stone has been captured within the basket, the slide 16 is then moved to the right in the view of FIG. 2 to move the sheath over at least a portion of the basket, thereby securely capturing the stone in the basket for removal.

On occasion, it may be necessary to remove the handle 12, the slide 16 and the sheath 18 while leaving the filament 22 and the basket 28 in place. This can readily be accomplished by unscrewing the cap 70 from the handle 12, removing the cap nut 74 from the parts 73, and then removing the parts 73, handle 12, slide 16 and sheath 18 from the filament 22.

Figure 7:
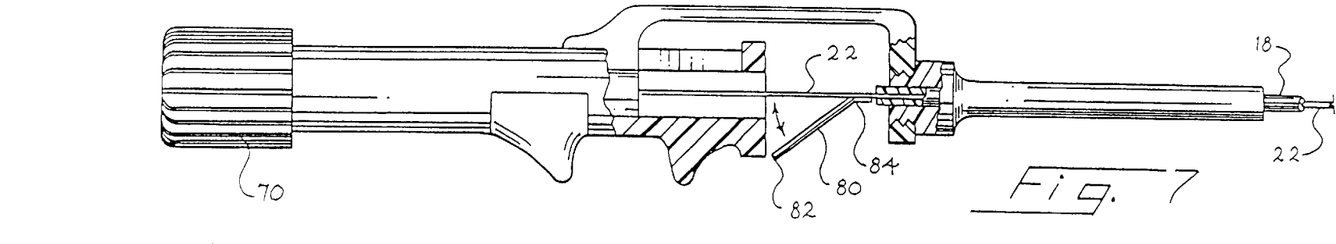
FIG. 7 is a cross-sectional view corresponding to that of FIG. 2 of a second preferred embodiment of this invention.
Figure 8:
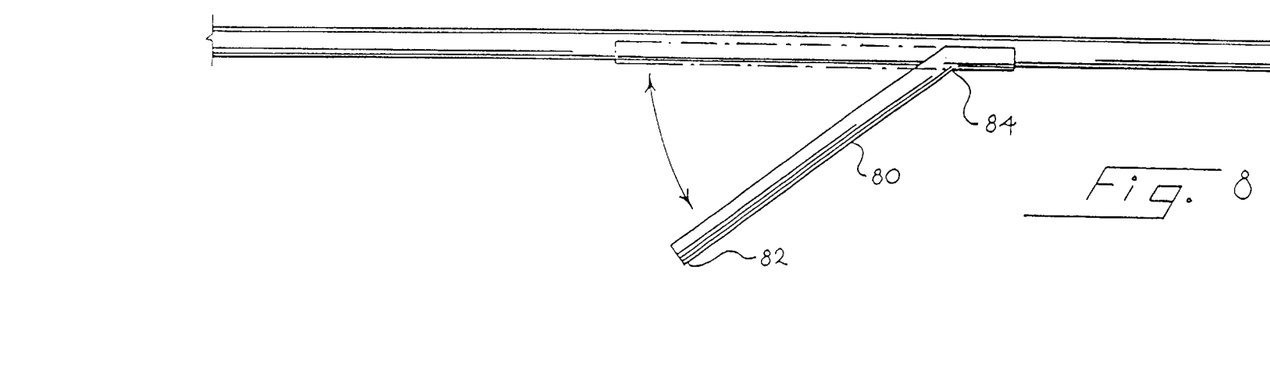
FIG. 8 is a fragmentary side view of selected elements of the embodiment of FIG. 7.

The disk 60 is an example of a manipulator used to rotate the filament 22 relative to the handle 12. This manipulator can take other forms, including the form shown in FIGS. 7 and 8. The embodiment of FIGS. 7 and 8 is similar to that of FIGS. 1 and 2, except that the disk 60 has been replaced by a lever 80. This lever 80 defines a free end 82 and hinged end 84, and the free end 82 is positioned closer to the first end 24 of the filament 22 than is the hinged end 84. During normal use, the lever 80 is positioned as shown in FIG. 7 in an extended position. In this position the user can apply torques to the lever 80 and therefore to the filament 22 to rotate the filament 22 as described above. The hinged end 84 is connected to the filament 22 at a hinged joint (e.g. a living hinge or a multiple-part hinge) and the lever 80 can be moved to the retracted position shown in dotted lines in FIG. 8. In this retracted position, the lever 80 can be moved through the lumen of the sheath 18, thereby allowing the handle, slide and sheath to be removed from the filament 22 as described above.

The Stone Extraction Basket

Figure 9:
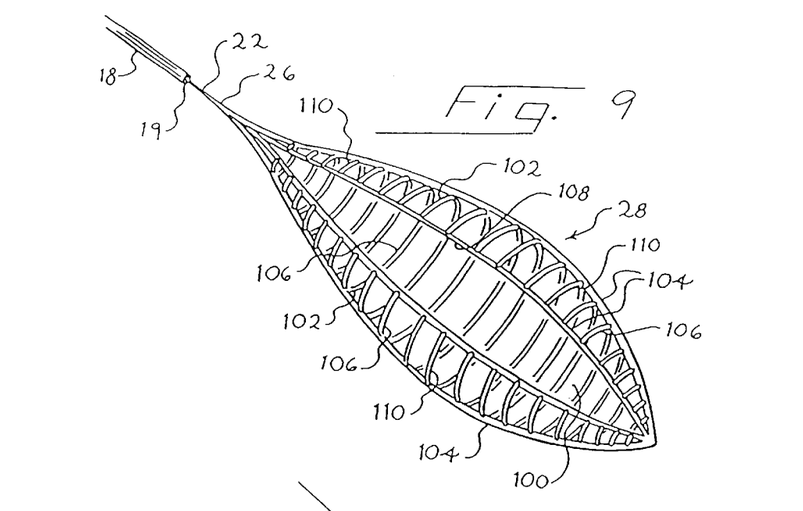
FIGS. 9, 10 and 11 are enlarged perspective views of three stone retention baskets suitable for use in the embodiments of FIGS. 1–8.

The stone extraction basket 28 of FIG. 9 is well adapted for use as a calaceal stone extraction basket, and also in the ureter when appropriate. This basket includes a stone entrance region 100 and a stone retention region 102. The retention region 102 extends over more than half the area of the basket. This basket is formed by a set of longitudinal basket wires 104 and a set of lateral basket wires 106. The longitudinal basket wires 104 form a larger opening 108 in the stone entrance region 100, and the basket wires 104, 106 cooperate to form a number of smaller openings 110 in the stone retention region 102. In this embodiment, the larger opening 108 is sized to admit a stone that is at least two millimeters in diameter, and the smaller openings 110 are sized to retain a stone smaller than two millimeters in diameter. In one example, the larger opening is sized to admit stones as large as 5 mm in diameter. The wires 104, 106 are preferably small, flexible, kink-resistant wires that are capable of collapsing together to fit within the lumen 19.

In FIG. 9 the basket is shown in its operational configuration in which the basket is fully outside of the lumen 19 of the sheath 18. As described above, after a stone has been captured within the basket of FIG. 9, the sheath 18 can be moved over part of the basket 28 to reduce the size of the larger opening 108. The basket 28 can also be used to capture ureteral stone fragments.

It should be noted that the larger opening 108 faces laterally with respect to a longitudinal basket axis extending through the second end 26 of the filament 22. Because the larger opening 108 is laterally facing, the filament rotating features of the handle 12 described above can be used to orient the larger opening 108 as desired to facilitate stone capture. Also, in the event a stone is captured that is too large to be removed from the body, the basket can be rotated to point the larger opening 108 downwardly. In this orientation, the weight of the stone tends to move it out of the basket. Once this occurs, the basket can be removed from the body and the stone fragmented using conventional lithothripsy techniques.

Figures 10, 11:
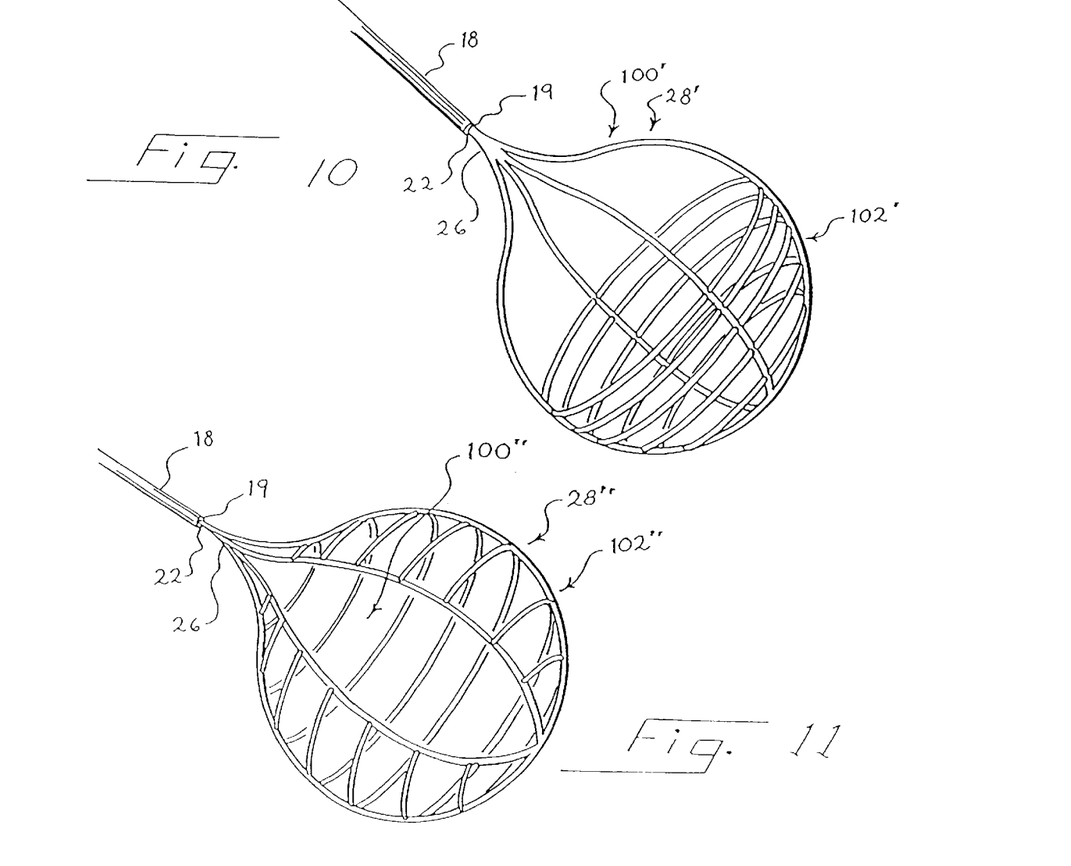

The basket 28' of FIG. 10 is similar to the basket 28 of FIG. 9 except that the stone entrance region 100' is positioned adjacent the second end 26 of the filament 22, and the stone retention region 102' is positioned opposite the second end 26 of the filament 22. The basket 28' is well suited for the collection of ureteral stone fragments after laser, ultrasonic, or electro-hydraulic lithothripsy. Also, the basket 28' may be positioned proximally of a stone prior to lithothripsy to prevent stone fragments from migrating up the ureter. In use, the collapsed basket 28' is moved past the stone or stones to be collected, then the sheath 18 is moved to allow the basket 28' to expand to the operational configuration of FIG. 10, and then the basket 28' is moved to collect the stones in the stone retention region. At this point, the sheath 18 is moved over the filament 22 to collapse the basket 28' partially, thereby retaining the captured stones in the stone retention region 102'.

FIG. 11 shows a basket 28" that is similar to the basket 28 of FIG. 9 including a stone entrance region 100" and a stone retention region 102". The main difference is that the basket 28" is shaped differently as appropriate for use as a percutaneous stone extraction basket.

The wires 104, 106 may be formed continuously with the filament 22, or alternately they may be secured to the filament 22. A variety of materials can be used for the wires 104, 106, but they should be sufficiently small in diameter, flexible and kink-resistant to allow the baskets 28, 28', 28" to be collapsed into the lumen 19. Super-elastic alloys such as the shape memory metal alloys described in U.S. Pat. No. 5,989,266 are suitable. One such shape-memory material is nitinol, which can be annealed as described in this patent. Other materials known to those skilled in the art, including various polymers, plastics and metal alloys, can readily be used to form filaments for the baskets 28, 28', 28", and these filaments can be arranged in any desired combination of longitudinal and/or transverse or oblique patterns. For example, the stone retention region may be formed in whole or in part by a net or mesh. The junction between adjacent wires in the baskets 28, 28', 28" can be secured in any suitable way, including sutures, adhesives, and knots of the type described in U.S. Pat. No. 5,989,266.

Figure 12:
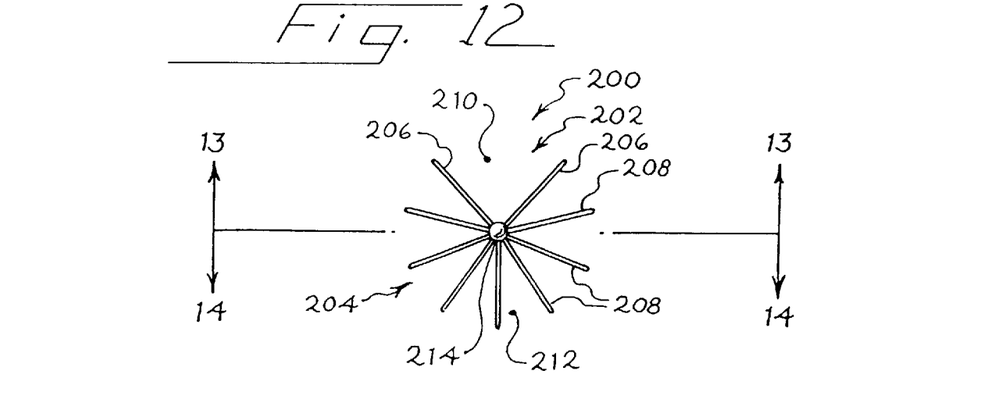
FIG. 12 is an end view of another stone retention basket suitable for use in the embodiments of FIGS. 1–8.
Figure 13:
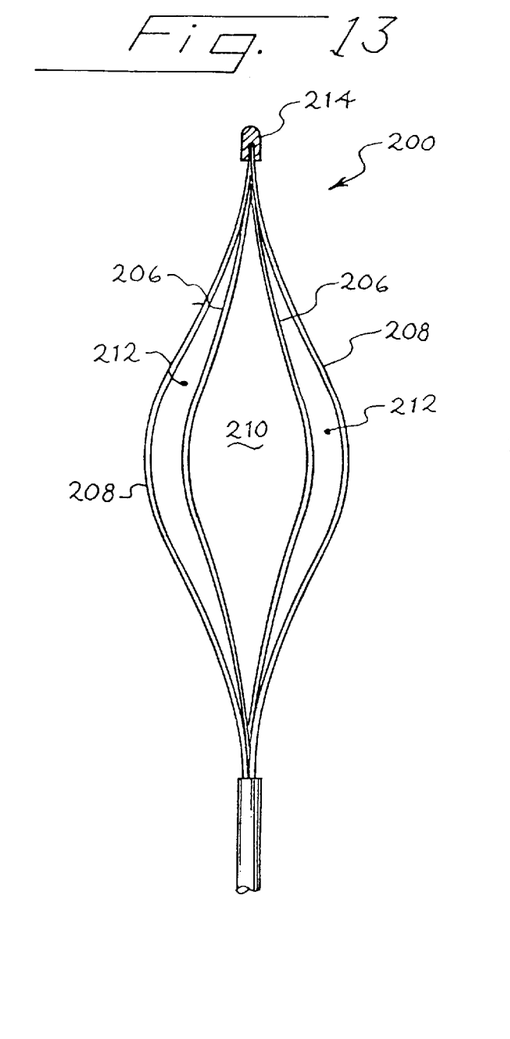
FIG. 13 is a cross-sectional view taken along line 13—13 of FIG. 12.
Figure 14:
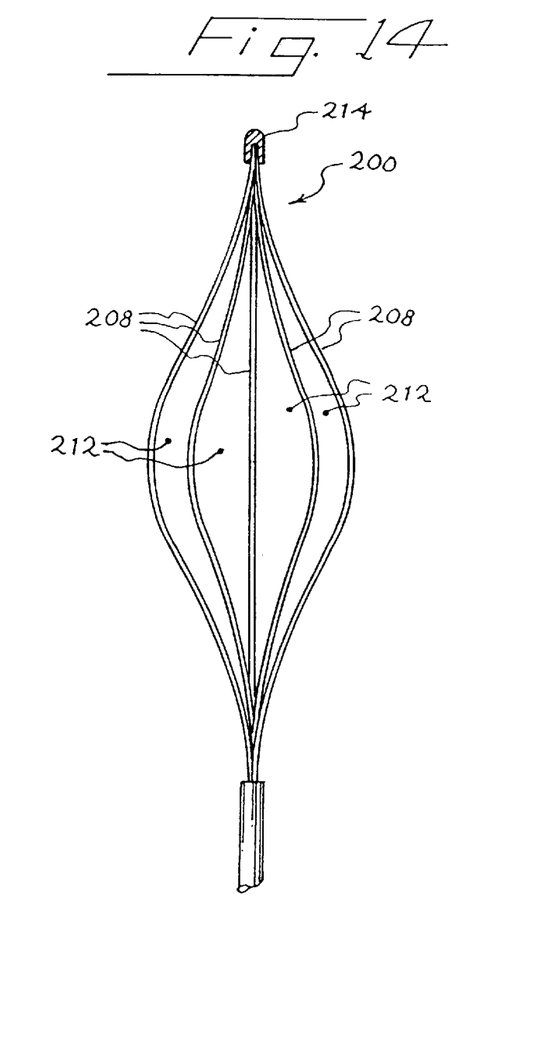
FIG. 14 is a cross-sectional view taken along line 14—14 of FIG. 12.

FIGS. 12–14 illustrate another stone retention basket 200 that is similar in general configuration to the basket 28 of FIG. 9. As best shown in FIG. 12, the basket 200 includes a stone entrance region 202 and a stone retention region 204. In general, the stone retention region 204 extends over more than one-half of the area of the basket 200. In this particular example, the stone entrance region extends over an arc of about 90°, and the stone retention regions extends over an arc of about 270°. Generally, it is preferred that the stone retention region extend over a continuous arc of greater than 180°, more preferably over a continuous arc of at least 250°, and most preferably over a continuous arc of 270° of the circumference of the basket 300.

The basket 200 is formed by a pair of longitudinal basket wires 206, and a plurality of longitudinal basket wires 208. The wires 206 border the stone entrance region 202, and the wires 208 are disposed in the stone retention region 204. As shown in FIG. 13, all of the wires 206, 208 of the basket 200 in this example extend longitudinally.

The basket wires 206 form a larger opening 210 in the stone entrance region 202, and the wires 206, 208 cooperate to form a number of smaller openings 212 in the stone retention region 204. FIGS. 12 and 13 show the manner in which the larger opening 210 is substantially larger than any of the smaller openings 212 on the front side of the basket. FIG. 14 shows that only the smaller openings 212 are found on the back side of the basket 200. In this embodiment, the larger opening 210 is sized to admit a stone that is at least 2 mm in diameter, and the smaller openings 212 are sized to retain a stone smaller than 2 mm in diameter. In one example, the larger opening 210 is sized to admit stones as large as 5 mm in diameter. The wires 206, 208 are preferably small, flexible, kink-resistant wires that are capable of collapsing together to fit within the lumen 19.

The wires 206, 208 are secured together at the distal end of the basket 200 by a tip 214. The tip 214 may be welded, soldered, swaged or otherwise held in place to secure the distal ends of the wires 206, 208 together. The following U.S. Patents describe various types of tips that can be used for this purpose: U.S. Pat. Nos. 4,612,931; 5,496,330; 5,957,932; 6,077,274; 6,093,196; and 6,190,394. The wires 206, 208 may also be held in place at the distal end of the basket in other ways that do not use a tip, as known to those skilled in the art.

Figure 15:
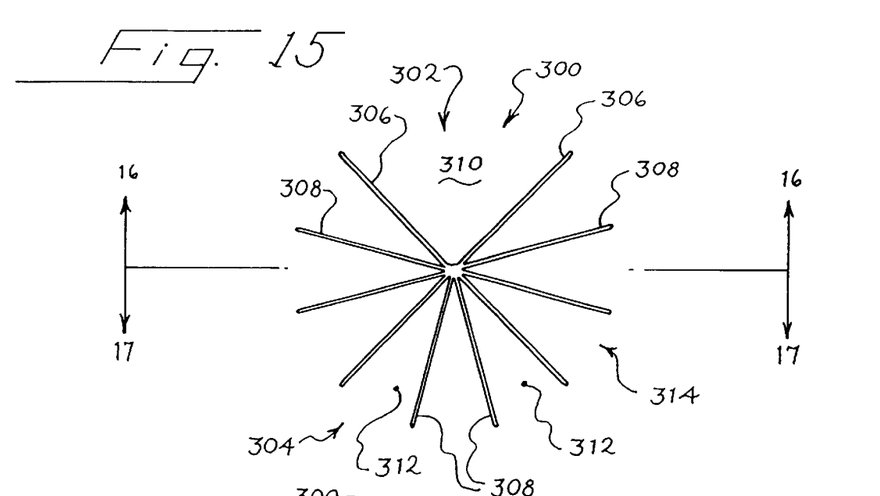
FIG. 15 is an end view of another stone retention basket suitable for use in the embodiments of FIGS. 1–8.
Figures 16, 17:
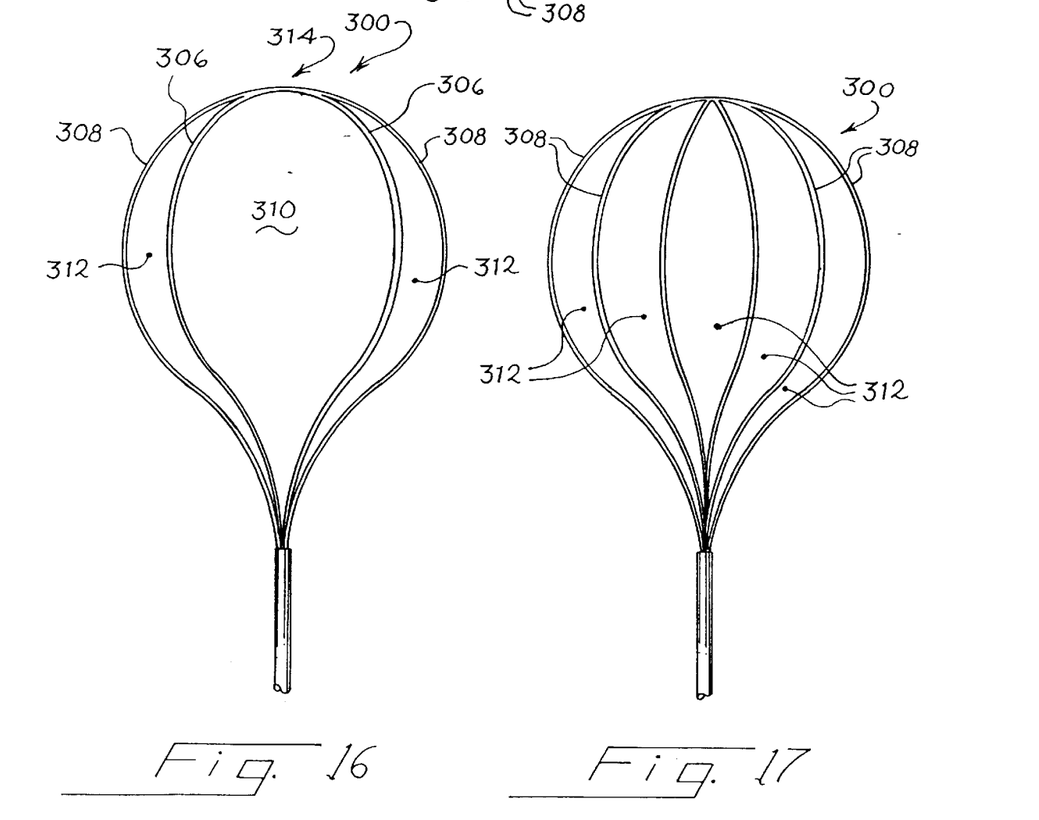
FIG. 16 is a cross-sectional view taken along line 16—16 of FIG. 15.
FIG. 17 is a cross-sectional view taken along line 17—17 of FIG. 15.

FIGS. 15–17 illustrate another stone retention basket 300 that is in many ways similar in general configuration to the basket 28" of FIG. 11. The basket 300 includes a stone entrance region 302 and a stone retention region 304. The stone entrance region 302 is bounded by two longitudinal basket wires 306, and a plurality of longitudinal basket wires 308 are positioned in the stone retention region 304. The longitudinal basket wires 306 bound a larger opening 310, and the wires 306, 308 define a plurality of smaller openings 312 configured to retain a stone in the basket. FIG. 16 shows that the larger opening 310 is substantially larger than any of the smaller openings 312 on the front side of the basket 300, and FIG. 17 shows that only the smaller openings 312 are found on the back side of the basket 300. As before, the stone retention region 304 in which the smaller openings 312 are found covers more than one-half of the total area of the basket 300 (about 75% of the total area in this example). Also, the stone retention region extends over a continuous arc of more than 180° (more preferably at least 250° and about 270° in this example). The wires 306, 308 are secured together in a looped or tied region 314, using for example techniques described in Foster U.S. Pat. No. 5,989,266 or similar techniques of the prior art.

The baskets 200, 300 described above can be used in substitution for the baskets of FIGS. 9 and 11, respectively. The baskets 200, 300 differ most importantly from those of FIGS. 9 and 11 in that they avoid the use of transversely extending wires or filaments, and they thereby simplify fabrication. Of course, other techniques can be used to secure the longitudinal basket wires together at the distal end, including the swaged pin technique and the slotted cap described in Kordis U.S. Pat. No. 6,216,044. Any of the materials described above in connection with the baskets 28, 28', 28" can be used for the baskets 200, 300.

The number of longitudinal basket wires 104, 208, 308 can be varied with the application, and 2, 3, 4, 5, 6 or more longitudinal wires can be used.

For the reasons discussed above, it is preferred to use the baskets 28, 28', 28" 200, 300 with the handle 12 of FIGS. 1 and 2. However, it should be clearly understood that the baskets of this invention are not limited to use with any particular handle, and a wide variety of handles can be used.

Stone Rakes

In the embodiments described above, a stone extraction basket is provided to capture and remove stones from the body. As an alternative, collapsible rakes can be used as an aid to collecting and withdrawing stones and stone fragments from the body. Such rakes are expected to provide substantial advantages in the removal of small stones and stone fragments.

FIGS. 18–21 relate to a collapsible rake 400 that is mounted to a first end portion 408 of a support filament 406 to move axially into and out of the lumen 404 of a sheath 402. The sheath 402 can be similar to the sheaths described above, and the support filament 406 can be manipulated relative to the sheath 402 by a handle 12 such as that described above. Such a handle allows the sheath 402 to be moved longitudinally relative to the rake 400 and the rake 400 to be rotated relative to the sheath 402.

Figure 18:
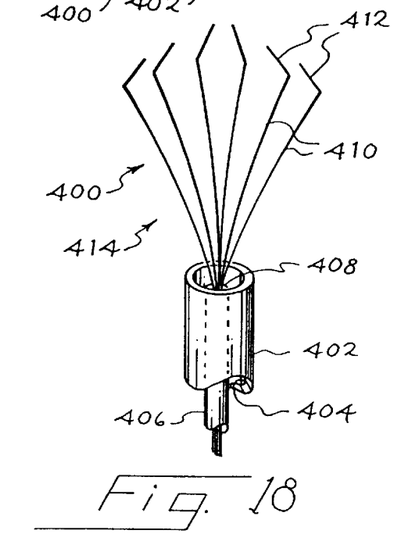
FIGS. 18, 19 and 20 are perspective, side and top views, respectively, of a collapsible rake in a first, extended position.
Figure 19:
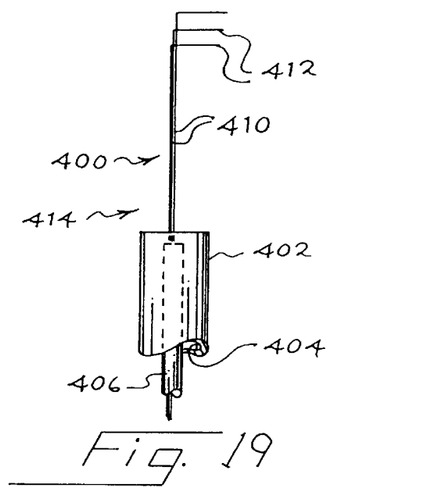
Figure 20:
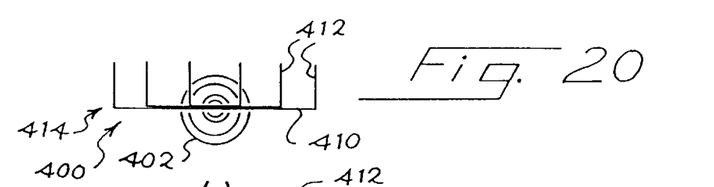

FIGS. 18–20 show the rake 400 in a first, extended position 414, in which the sheath 402 has been withdrawn so that the rake 400 is positioned outside of the lumen 404. As best shown in FIG. 18, the rake 400 includes multiple shafts 410, each terminating at its distal end in a respective raking portion 412. In this example, each raking portion 412 is formed as a bent distal end of the respective shaft 410. The raking portions are smoothly rounded at the exposed end to reduce tissue damage. In some cases a rounded ball may be secured or formed on the exposed end to further blunt the raking portions. FIG. 19 shows a side view of the rake 400 in the first position 414, and it can be seen from FIG. 19 that the raking portions 412 all extend laterally to the longitudinal axis of the support filament 406. The top view of FIG. 20 clarifies the orientation of the raking portions 412.

Figure 21:
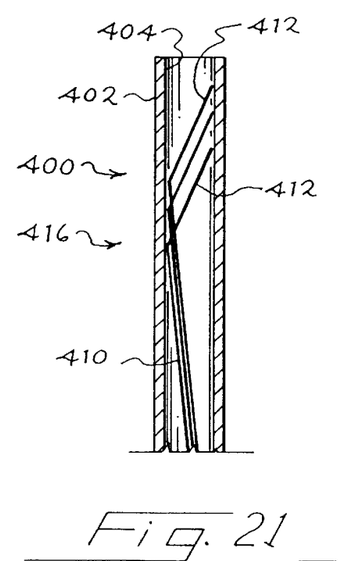
FIG. 21 is a cross-sectional view of portions of the rake of FIGS. 18–20 in a second, retracted position.

In order to facilitate insertion of the rake 400 into a body lumen, the rake 400 can be collapsed into the lumen 404 of the sheath 402 by moving the rake 400 to the second position 416 shown in FIG. 21. Note that the raking portions 412 are straightened to some extent so that both the shafts 410 and the raking portions 412 fit entirely within the lumen 404. Preferably, the shafts 410 are formed of a material of sufficient resilience to allow the raking portions 412 to return to the position of FIGS. 18–20 when the raking portions 412 are outside of the lumen 404.

Figure 22:
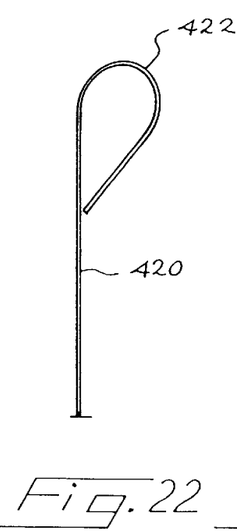
FIG. 22 is a side view of a portion of a second rake.
Figure 23:
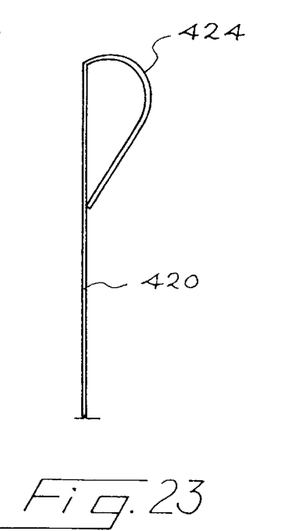
FIG. 23 is a side view of a portion of a third rake.

FIGS. 22 and 23 show alternative forms of the rake shaft and raking portion. In the example of FIG. 22, the shaft 420 terminates in a loop-shaped raking portion 422. The example of FIG. 23 is similar, but in this case the loop portion 424 is joined to the shaft 420 at an angle rather than the smooth transition of the raking portion 422.

In use, the rake 400 is first positioned within the sheath 402 as illustrated in FIG. 21, and then the sheath 402 is inserted in a body cavity or lumen to a point beyond the position of the stone or stone fragments to be removed. The support filament 406 can be rotated to place the rake 400 in the desired orientation, and the sheath 402 is then withdrawn, thereby exposing the rake 400. The rake 400 then automatically deploys to the extended position shown in FIGS. 18–20. In this position the raking portions 412 and the sheath 402 can be positioned on opposite sides of the stones or stone fragments to be removed. Then the sheath 402, the filament 406, and the rake 400 are withdrawn as a unit, and the rake 400 is used to pull stones and stone fragments out of the body. Preferably, the raking portions 412, 422, 424 are sufficiently resilient that they can bend away from the sheath 402 when an obstruction is encountered, thereby improving the safety of the rake 400 and reducing any injury to body tissues.

The shafts 410, 420 can be formed continuously with the filament 406, or alternatively they may be secured to the filament 406. A variety of materials can be used for the shafts 410, 420 and the raking portions 412, but the shafts 410, 420 should be sufficiently small in diameter, flexible and kink-resistant to allow the rake 400 to be collapsed into the lumen 404. Super elastic alloys such as shape memory metals including nitinol are suitable. Other materials including various polymers, plastics and metal alloys can be used. If desired, transversely extending elements (not shown) can be provided between the shafts 410 to limit the maximum separation of the adjacent raking portions 412, 422, 424 when the rake 400 is deployed to the first position.

Though it is preferred to use the rake 400 with the handle 12 of FIGS. 1 and 2, it should be clearly understood that the rakes of this invention are not limited to use with any particular handle, and a wide variety of handles can be used.

Conclusion

It should be apparent from the foregoing detailed description that improved endoscopic stone extraction devices have been described that are well suited to the collection of a wide variety of stones, including stone fragments. The rakes described above are well suited to the removal of many types of debris, including for example, stones, stone fragments, and cholesterol plaque fragments. The devices described above can be used with the widest variety of endoscopes, including ureteroscopes, nephroscopes and other endoscopic devices, and they can be used within the lumens of many body tissues, including for example, ureters, bile ducts, and blood vessels.

As used herein, the term "stone" is intended broadly to encompass a wide variety of biological stones, calculus and the like, including fragments of stones, calculus and the like formed by any of the techniques described above or other techniques developed in the future. Urinary tract stones and biliary tract stones are two examples.

The term "end portion" is intended broadly to encompass the end of structure such as a filament along with an adjacent portion of the structure.

The term "surface" is intended broadly to encompass perforated surfaces.

The term "filament" is intended broadly to encompass wires and other elongated structures formed of any of a wide range of materials, including metals, plastics, and other polymers.

The foregoing detailed description has discussed only a few of the many forms that this invention can take. For this reason, this detailed description is intended by way of illustration and not limitation. It only the following claims, including all equivalents, that are intended to define the scope of this invention.

What is claimed is:

1. An endoscopic stone-extraction device comprising:
    a support filament comprising a first end portion and a second end portion;

a sheath comprising a lumen, the support filament disposed in the lumen such that the sheath is slideable with respect to the support filament;

a stone-extraction basket carried by the first end portion of the support filament;

a handle comprising an actuator, wherein movement of the actuator in a first direction advances the sheath and causes the basket to at least partially collapse inside the lumen of the sheath, and wherein movement of the actuator in a second direction retracts the sheath and causes the basket to expand to an operational shape outside the lumen of the sheath;

the basket comprising a stone-entrance region and a stone-retention region, the stone-entrance region comprising a first, larger opening sized to admit a stone into the basket, the stone-retention region comprising a plurality of second openings, all of the second openings being smaller than the first opening;

the first opening facing laterally away from a longitudinal axis extending through the basket and passing through the first end portion of the support filament, the stone-retention region extending over more than one-half of a total surface area defined by the basket.

2. The invention of claim 1 wherein the basket comprises a set of longitudinal basket filaments radiating from the first end portion of the support filament and a set of lateral basket filaments extending between the longitudinal basket filaments, the lateral basket filaments positioned substantially entirely in the stone-retention region of the basket.

3. The invention of claim 1 wherein the second openings are all smaller than 2 mm in minimum dimension.

4. The invention of claim 3 wherein the first opening is larger than 2 mm in minimum dimension.

5. The invention of claim 1 wherein the basket is configured to collapse into the lumen when the basket is moved into the lumen, and to expand to the operational shape when the basket is moved out of the lumen.

6. The invention of claim 1 wherein the filament and basket are free of attachment to the sheath, such that the entire basket is movable into the lumen of the sheath.

7. The invention of claim 1 wherein the basket comprises a set of longitudinal basket filaments radiating from the first end portion of the support filament, the set of filaments comprising a pair of first filaments that border the stone entrance region and a plurality of second filaments disposed in the stone retention region, the second openings defined by the first and second longitudinal filaments.

8. The invention of claim 7 wherein the first opening is bounded by the first filaments, and wherein all of the second openings are entirely formed by the first and second filaments.

9. The invention of claim 1 wherein the stone retention region extends over at least three quarters of the total surface area defined by the basket.

10. The invention of claim 1 wherein the stone retention region extends over a continuous arc of at least 180° of a circumference of the basket.

11. The invention of claim 1 wherein the stone retention region extends over a continuous arc of at least 250° of a circumference of the basket.

12. The invention of claim 1 wherein the basket comprises at least three longitudinal basket filaments radiating from the first end portion of the support filament.

13. The invention of claim 1 wherein the second openings are all smaller than 5 mm in minimum dimension.

14. An endoscopic stone-extraction device comprising:

a support filament comprising a first end portion and a second end portion;

a sheath comprising a lumen, the support filament disposed in the lumen such that the sheath is slideable with respect to the support filament;

a stone-extraction basket carried by the first end portion of the support filament;

a handle comprising an actuator, wherein movement of the actuator in a first direction advances the sheath and causes the basket to at least partially collapse inside the lumen of the sheath, and wherein movement of the actuator in a second direction retracts the sheath and causes the basket to expand to an operational shape outside the lumen of the sheath;

the basket comprising a stone-entrance region and a stone-retention region, the stone-entrance region comprising a first, larger opening sized to admit a stone into the basket, the stone-retention region comprising a plurality of second openings, all of the second openings being smaller than the first opening;

the first opening facing laterally away from a longitudinal axis extending through the basket and passing through the first end portion of the support filament;

the stone-retention region extending over a continuous arc of greater than 180°.

15. The invention of claim 14 wherein the stone-retention region extends over a continuous arc of greater than 250°.

16. The invention of claim 14 wherein the stone-retention region extends over a continuous arc of greater than 270°.

17. The invention of claim 14 wherein the basket comprises at least three longitudinal basket filaments radiating from the first end portion of the support filament.

* * * * *